United States Patent [19]

Ingelman et al.

[11] 4,201,772

[45] May 6, 1980

[54] STERILE AQUEOUS SOLUTION OF A MIXTURE OF ISOMALTO-OLIGOSACCHARIDES AND ITS USE FOR PARENTERAL ADMINISTRATION TO MAMMALS

[75] Inventors: Björn G. Ingelman; Ary W. Richter; Kirsti A. Granath, all of Upsala, Sweden

[73] Assignee: Pharmacia Aktiebolag, Upsala, Sweden

[21] Appl. No.: 891,106

[22] Filed: Mar. 28, 1978

[30] Foreign Application Priority Data

Apr. 19, 1977 [GB] United Kingdom ............... 16162/77

[51] Int. Cl.² ..................... A61K 31/70; A61K 31/715
[52] U.S. Cl. ........................................ 424/180; 536/51; 536/112
[58] Field of Search ................... 536/112, 51; 424/180

[56] References Cited

U.S. PATENT DOCUMENTS 2,708,174  5/1955  Stavely ................................. 536/112

OTHER PUBLICATIONS

Richter, W., J. Immun. vol. 107 (1971), 948–952.
Richter, W., Int. Arch. Allergy, vol. 41 (1971), 826.
Richter, W., Int. Arch. Allergy, vol. 43 (1972), 1–16.
Richter, W., Int. Arch. Allergy, vol. 45 (1973), 930–936.

Primary Examiner—Johnnie R. Brown
Assistant Examiner—Blondel Hazel

Attorney, Agent, or Firm—Fred Philpitt

[57] ABSTRACT

A sterile aqueous solution containing 0.02 to 30 g per 100 ml solution of a mixture of isomalto-oligosaccharides comprising (a) 0–15 percent by weight of isomaltose, (b) 20–65 percent by weight of isomaltotriose, isomaltetraose and isomaltopentaose, each of these oligosaccharides being present in an amount of at least 5 percent by weight and at most 25 percent by weight, (c) 20–65 percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight, 0–30 percent by weight of said mixture being isomaltooligosaccharides of 10 to 20 glucose units and 0–10 percent by weight of said mixture being isomaltooligosaccharides of 15 to 20 glucose units, the percentages being calculated on the total weight of the mixture of isomalto-oligosaccharides, and the use of said sterile aqueous solution for parenteral administration to mammals closely prior to or contemporaneously with the parenteral administration of clinical dextran to reduce the risks for adverse effects of the clinical dextran.

26 Claims, No Drawings

STERILE AQUEOUS SOLUTION OF A MIXTURE OF ISOMALTO-OLIGOSACCHARIDES AND ITS USE FOR PARENTERAL ADMINISTRATION TO MAMMALS

The present invention relates to sterile aqueous solutions for parenteral administration containing a carbohydrate-containing substance and to a carbohydrate-containing substance to be used in the preparation of such sterile aqueous solution. The invention also relates to methods for the preparation of said solutions and said carbohydrate-containing substance.

Carbohydrate-containing substances consisting of individual isomalto-oligosaccharides, e.g. isomaltose, isomaltotriose, isomaltotetraose, isomaltopentaose, isomaltohexaose, isomaltoheptaose, isomaltooctaose, isomaltononaose or isomaltodecaose, are previously known. They have preferably been isolated from partial hydrolysates of dextran. Mixtures of isomalto-oligosaccharides are also known e.g. in the form of partial hydrolysates of dextran. It is previously known that such substances may react as haptens with antibodies against dextran but no product which could be used in practice has been available.

According to the present invention, however, a very particularly selected mixture having a particular new composition of isomalto-oligosaccharides as will be disclosed more in detail below is made use of which mixture has particular combination of favourable properties for use in sterile aqueous solutions for parenteral administration, preferably for injection or infusion in blood vessels, and which can be manufactured industrially in a large scale and be used in practice.

Solutions according to the invention comprising this particular isomalto-oligosaccharide mixture may be given intravenously in great amounts without any harmful influence upon the kidneys and without other harmful effects, a mild osmotic diuretic effect hereby being obtained. This particular isomalto-oligosaccharide mixture does not give rise to flakes or other particulate precipitations in the solutions. It may exist in combination with clinical dextran in the solution without increasing the tendency of the dextran to form flakes in the solution. (Especially in combination with low-molecular hydrolysates of dextran there is under other circumstances a strong tendency of dextan to form flakes and particles in the solution.) To the contrary, this particular isomalto-oligosaccharide mixture has a stabilizing effect on dextran solutions so that their tendency of forming flakes is reduced on sufficient addition thereof. This specific isomalto-oligosaccharide mixture is also particularly selected to contemporaneously on parenteral administration be able to block different types of antibodies which are directed against dextran and which may occur in patients without said mixture itself causing reactions in patients which are hypersensitive to dextran because of having such antibodies. Hypersensitive individuals may by such blocking of said antibodies with said mixture be given dextran with less discomfort and risks.

Solutions according to the invention containing this particular isomalto-oligosaccharide mixture may be given parenterally, for instance before the start of infusion of solutions containing clinical dextran (e.g. having a weight average molecular weight $\overline{M}_w$ within the range 30,000 to 80,000) without this added ingredient. Solutions according to the invention containing this particular isomalto-oligosaccharide mixture as well as clinical dextran can be given parenterally with or without the above mentioned pre-treatment. Herewith the risks for adverse effects of the clinical dextran are reduced by hapten-blocking of antibodies, and by the mild osmotic diuretic effect which counteracts the formation of viscous urine after the administration of the clinical dextran.

The sterile aqueous solutions for parenteral administration (preferably solutions for injection or infusion) according to the invention are characterized in that they contain 0.01 to 35 g, preferably 0.03 to 30 g (especially 0.1 to 30 g, for example 0.2 to 30 g, e.g. 0.3 to 20 g), per 100 ml solution of a mixture of isomalto-oligosaccharides, said mixture of oligosaccharides comprising (a) 0–15 percent by weight of isomaltose,
(b) 20–65, preferably 20–60, percent by weight of isomaltotriose, isomaltotetraose and isomaltopentaose, each of these oligosaccharides being present in an amount of at least 5 percent by weight and at most 25 percent by weight,
(c) 20–65, preferably 20–60, percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight,
(d) 0–30, preferably 0–25, percent by weight of isomaltooligosaccharides of 10 to 20 glucose units, 0–10 percent by weight being isomalto-oligosaccharides of 15 to 20 glucose units, the percentages being calculated on the total weight of the mixture of isomalto-oligosaccharides.

The isomalto-oligosccharide mixture in the solution preferably comprises 0 to 10 percent by weight, for instance 2–10 percent by weight, of isomaltose.

Suitably at most 55 percent by weight of the isomalto-oligosaccharide mixture in the solution consist of isomaltotriose, isomaltotetraose and isomaltopentaose, for instance 25–55 percent by weight, such as 25–50 percent by weight, e.g. more than 30 and less than 50 percent by weight.

Suitably at least 25 percent by weight of the isomalto-oligosaccharide mixture in the solution consists of isomaltohexaose, isomaltoheptaose, isomaltooctaose and isomaltononaose, for instance 25–60 percent by weight, such as 25–55 percent by weight, e.g. more than 30 and less than 50 percent by weight. Suitably the total amount of isomaltohexaose and isomaltoheptaose exceeds 15 percent (for instance more than 20 percent) by weight of the oligosaccharide mixture.

Preferably isomaltopentaose and isomaltotetraose in the isomalto-oligosaccharide mixture in the solution are each present in said mixture in a greater amount than each of isomaltotriose and isomaltose. Preferably, isomaltohexaose and isomaltoheptaose are each present in a greater amount than each of isomaltononaose and isomaltodecaose.

Suitably, more than 60 percent by weight, such as more than 65 percent by weight (for instance more than 70 or 75 percent by weight) of said isomalto-oligosaccharide mixture in the solution consist of isomalto-oligosaccharides of 3 to 9 glucose units.

By way of example more than 50 percent by weight, e.g. more than 55 or 60 percent by weight, of said isomalto-oligosaccharide mixture in the solution may consist of isomalto-oligosaccharides of 4 to 8 glucose units.

Suitably 0–20, e.g. 5–20 or 5–15, percent by weight of the isomalto-oligosaccharide mixture in the solution consist of isomalto-oligosaccharides of 10 to 20 glucose units, 0–10, preferably 0–7, such as 0–5, percent by weight consisting of isomalto-oligosaccharides of 15 to 20 glucose units.

Examples of suitable isomalto-oligosaccharide mixtures in the solution according to the invention are for instance such mixtures comprising 0–12 (e.g. 2–10) percent by weight of isomaltose, 25–55 (e.g. 30–50) percent by weight of isomaltotriose, isomaltotetraose, and isomaltopentaose, 25–55 (e.g. 30–50) percent by weight of isomaltohexaose, isomaltoheptaose, isomaltooctaose and isomaltononaose, 5–20 (e.g. 5–18 or 5–15) percent by weight of isomalto-oligosaccharides of 10 to 20 glucose units, 0–7 percent by weight consisting of oligosaccharides of 15 to 20 glucose units.

The weight average molecular weight $\overline{M}_w$ of the isomalto-oligosaccharide mixture in the solution is preferably less than 1180, e.g. less than 1150, by way of example less than 1120 or 1100. It is by way of example higher than 720, e.g. higher than 750 or 800. Generally it is higher than 850, e.g. higher than 900. By way of example it lies within the range 1000–1100.

The number average molcular weight $\overline{M}_n$ of the isomaltooligosaccharide mixture in the solution may suitably be higher than 670, e.g. higher than 680, such as higher than 700. It may by way of example be less than 1000, e.g. less than 900, e.g. less than 850, such as less than 840, e.g. less than 820.

The solution according to the invention may also contain clinical dextran, i.e. dextran intended for parenteral administration such as for injection and infusion e.g. in blood vessels. In this connection, the solution according to the invention preferably contains per 100 ml of solution 0.01 to 10 g, e.g. 0.02 to 10 g, e.g. 0.2 to 10 g or 0.3 to 5 g, (especially 0.1 to 3 g, for example 0.2 to 2 g, e.g. 0.3 to 2 g or 0.5 to 2 g) of said isomalto-oligosaccharide mixture and 2 to 12 g of clinical dextran having a weight average molecular weight $\overline{M}_w$ within the limits 30,000 to 80,000 (calculated without the addition of the isomalto-oligosaccharide mixture). (Preferably, less than 8 (especially less than 6, for example less than 5, e.g. less than 4 or 3) percent by weight of said clinical dextran being in the molecular weight range below 10,000, i.e. before the admixture of the isomalto-oligosaccharide mixture.)

The solution according to the invention may per 100 ml of solution for instance contain 0.01 to 10 g, e.g. 0.02 to 5 g, (especially 0.1 to 3 g, for example 0.2 to 2 g, e.g. 0.3 to 2 g or 0.5 to 2 g) of said isomalto-oligosaccharide mixture and 4 to 8 g of Dextran 70 or Dextran 60. In this connection the solution may per 100 ml of solution contain less than 0.5 g, preferably less than 0.4 g, especially less than 0.3 g (e.g. less than 0.2 g) of molecules in the molecular weight range of 3000 to 10,000. Such improved dextran solutions have a low tendency of forming flakes.

By way of example the solution according to the invention may per 100 ml of solution contain 0.01 to 10 g, e.g. 0.02 to 5 g, (especially 0.1 to 3 g, for example 0.2 to 2 g, e.g. 0.3 to 2 g or 0.5 to 2 g) of said isomalto-oligosaccharide mixture and 8 to 12 g of Dextran 40. Also in this connection the solution may per 100 ml solution contain less than 0.5 g, preferably less than 0.4 g, such as less than 0.3 g (e.g. less than 0.2 g) of dextran molecules in the molecular weight range of 3000 to 10,000. Such improved dextran solutions have a low tendency of forming flakes. (Dextran 70, Dextran 60 and Dextran 40 are the pharmacopaeia designations for dextran preparations having $\overline{M}_w$-values of about 70,000, about 60,000 and about 40,000, respectively.)

The above mentioned solutions according to the invention may also contain other substances which are physiologically acceptable on parenteral administration, e.g. glucose and sodium chloride. The solution may per 100 ml of solution contain for instance 0.1 to 1 g of sodium chloride and/or 0.1 to 10, e.g. 0.1 to 5 g of glucose.

The invention also comprises a method for the preparation of the solutions according to the invention. According to said method the above mentioned isomalto-oligosaccharide mixture and optionally also additives used in the preparation of solutions for parenteral administration, such as sodium chloride, glucose or clinical dextran, and water are mixed in such proportions that when the substances are in solution the content of the isomalto-oligosaccharide mixture is within the limits stated above, whereafter the solution is filtered and poured into receptacles for solutions for parenteral use, e.g. glass bottles or plastics bags (e.g. measuring 10 to 1000 ml), which receptacles are then sealed and heat-sterilized. The contents of additives, when such are present, are within the limits conventionally used with respect to the respective substance in solutions for parenteral administration, for instance the limits given above.

The carbohydrate-containing substance according to the invention, which substance is intended to be used in the preparation of sterile aqueous solutions for parenteral administration (primarily solutions for injection or infusion) according to the invention, is characterized in that it consists of or contains a mixture of isomalto-oligosaccharides, said mixture of oligosaccharides comprising (a) 0–15 percent by weight of isomaltose,
(b) 20–65, preferably 20–60, percent by weight of isomaltotriose, isomaltotetraose and isomaltopentaose, each of these oligosaccharides being present in an amount of at least 5 percent by weight and at most 25 percent by weight,
(c) 20–65, preferably 20–60, percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight,
(d) 0–30, preferably 0–25, percent by weight of isomalto-oligosaccharides of 10 to 20 glucose units, 0–10 percent by weight being isomalto-oligosaccharides of 15 to 20 glucose units, the percentages being calculated on the total weight of the mixture of isomalto-oligosaccharides.

The isomalto-oligosaccharide mixture preferably contains at most 10 percent by weight of isomaltose, for instance 2–10 percent by weight.

Suitably at most 55 percent by weight of the isomaltooligosaccharide mixture consist of isomaltotriose, isomaltotetraose and isomaltopentaose, for instance 25–55 percent by weight, such as 25–50 percent by weight, e.g. more than 30 and less than 50 percent by weight.

Suitably at least 25 percent by weight of the isomaltooligosaccharide mixture consist of isomaltohexaose, isomaltoheptaose, isomaltooctaose and isomaltononaose, for instance 25–60 percent by weight, such as 25–55 percent by weight, e.g. more than 30 and less than 50 percent by weight. Suitably the total amount of isomaltohexaose and isomaltoheptaose exceeds 15 percent (e.g. more than 20 percent) by weight of the oligosaccharide mixture.

Preferably isomaltopentaose and isomaltotetraose are each present in a greater amount than each of isomaltotriose and isomaltose. Preferably isomaltohexaose and isomaltoheptaose are each present in a greater amount than each of isomaltononaose and isomaltodecaose.

Suitably, more than 60 percent by weight, such as more than 65 percent by weight (for instance more than 70 or 75 percent by weight) of said isomalto-oligosaccharide mixture consist of isomalto-oligosaccharides of 3 to 9 glucose units.

By way of example more than 50 percent by weight, e.g. more than 55 or 60 percent by weight, of said isomalto-oligosaccharide mixture may consist of isomalto-oligosaccharides of 4 to 8 glucose units.

Suitably 0–20, e.g. 5–20 or 5–15, percent by weight of the isomalto-oligosaccharide mixture consist of isomalto-oligosaccharides of 10 to 20 glucose units, 0–10, preferably 0–7 such as 0–5, percent by weight consisting of isomalto-oligosaccharides of 15 to 20 glucose units.

Examples of suitable isomalto-oligosaccharide mixtures according to the invention are for instance such mixtures comprising 0–12 (e.g. 2–10) percent by weight of isomaltose, 25–55 (e.g. 30–50) percent by weight of isomaltotriose, isomaltotetraose and isomaltopentaose, 25–55 (e.g. 30–50) percent by weight of isomaltohexaose, isomaltoheptaose, isomaltooctaose and isomaltononaose, 5–20 (e.g. 5–18 or 5–15) percent by weight of isomalto-oligosaccharides of 10 to 20 glucose units, 0–7 percent by weight consisting of isomalto-oligosaccharides of 15 to 20 glucose units.

The weight average molecular weight $\overline{M}_w$ of the isomalto-oligosaccharide mixture is preferably less than 1180, e.g. less than 1150, by way of example less than 1120 or 1100. It is by way of example higher than 720, e.g. higher than 750 or 800. Generally it is higher than 850, e.g. higher than 900. By way of example it lies within the range 1000–1100.

The number average molecular weight $\overline{M}_n$ of the isomalto-oligosaccharide mixture may suitably be higher than 670, e.g. higher than 680 such as higher than 700. It may by way of example be less than 1000, e.g. less than 900, e.g. less than 850 such as less than 840, e.g. less than 820.

The carbohydrate-containing substance according to the invention may also contain other substances which are physiologically acceptable on parenteral administration, e.g. glucose, sodium chloride and clinical dextran. The isomalto-oligosaccharide mixture may per 1 part by weight of said mixture contain for instance 0 to 1 parts by weight of glucose, such as 0.01 to 0.1 (e.g. 0.01 to 0.05) parts by weight of glucose. The oligosaccharide mixture may per 1 part by weight of said mixture contain for instance 0 to 0.1 (e.g. 0 to 0.03 or 0.001–0.01) parts by weight of sodium chloride.

Said isomalto-oligosaccharide mixture may be admixed to clinical dextran having a weight average molecular weight $\overline{M}_w$ of 30,000 to 80,000 (e.g. Dextran 70, Dextran 60 and Dextran 40). (Preferably, less than 8 (especially less than 6, for example less than 5, e.g. less than 4 or 3) percent by weight of said clinical dextran being in the molecular weight range below 10,000, i.e. before the admixture of the isomalto-oligosaccharide mixture.) For example, 1 part by weight of the isomalto-oligosaccharide mixture may be admixed with 0.5 to 500, preferably 1 to 300, especially 1 to 100, for example 1 to 60 (for example 1 to 50, e.g. 3 to 30) parts by weight of said clinical dextran. The carbohydrate-containing substance may, by way of example, consist of 0.3 to 50, for example 0.5 to 40, such as 1 to 30, e.g. 3 to 30, such as 5 to 20, e.g. 5 to 10 percent by weight of said isomalto-oligosaccharide mixture, the balance being said dextran and possibly small amounts of glucose and sodium chloride (for example 0–5, e.g. 0–2, such as 0–1 percent by weight). Said mixture of isomalto-oligosaccharides and clinical dextran may advantageously contain less than 8, preferably less than 6, especially less than 5, such as less than 4 or less than 3 percent by weight of molecules within the molecular weight range of 3000 to 10,000.

The particular mixture of isomalto-oligosaccharides which is made use of in the present invention may be obtained by mixing the individual oligosaccharides in proportions such that the desired mixture is obtained. However, it is practically and economically best obtained from partial hydrolysates of dextran, which are obtained e.g. by acid or enzymatic hydrolysis, hydrolysates containing isomalto-oligosaccharides being fractionated up e.g. by means of fractionated precipitation and/or dissolution (e.g. in mixtures of water and a precipitation agent such as ethanol, methanol or acetone) and/or by means of gel chromatographic separation and/or adsorption separation and/or ultrafiltration and such separated fractions being combined in such a way that the particular desired mixture of isomalto-oligosaccharides is obtained. Such a fraction may also be adjusted as to its composition by adding one or more of the individual oligosaccharides.

The invention also relates to a method for the preparation of the carbohydrate-containing substance containing the particular mixture of isomalto-oligosaccharides defined above. The method is characterized in that dextran is hydrolyzed partially to one or more hydrolysates containing a mixture of isomalto-oligosaccharides in the range of 2 to 20 glucose units and that isomalto-oligosaccharide-containing fractions are isolated from such hydrolysates by fractionation and optionally combined in proportions to give an isomalto-oligosaccharide mixture having the composition given above.

The dextran may advantageously be prepared by means of Leuconostoc mesenteroides, strain NRRL B-512. As the starting dextran for the above mentioned partial hydrolysis dextran fractions having $\overline{M}_w$-values in the range, for example 5000–30,000, such as 10,000–30,000, e.g. 13,000–22,000, may advantageously be used. The partial hydrolysis of dextran is advantageously driven in one or more steps so far that the hydrolysate contains a comparatively small part of isomalto-oligosaccharides of 10 and more glucose units (e.g. less than 20, such as less than 15, e.g. less than 10 or 5 percent by weight calculated on the total weight of the hydrolysate) so that later a fraction, which is precipitating first on precipitation with ethanol, may be recovered and made use of. It has appeared possible to carry out the necessary fractionation of the hydrolysates technically by means of precipitation with ethanol and treatment with active carbon. (The adsorption of the isomalto-oligosaccharides on carbon is dependent on the molecular weight.) By combining, in suitable proportions, suitable fractions thus obtained to carbohydrate-containing substance containing a mixture of isomalto-oligosaccharides having the composition given above a well reproducable product may be prepared on a technical scale.

The invention also comprises a method of improving clinical dextran having a weight average molecular weight ($\overline{M}_w$) within the range 30,000 to 80,000 with respect to side effects on parenteral administration, which method is characterized in that said clinical dextran is admixed with a mixture of isomalto-oligosaccharides as specified above, the proportions between said mixture and said clinical dextran being 1 part by weight of said mixture to 0.5 to 500, preferably 1 to 300, parts by weight of said clinical dextran, e.g. 1 to 100 parts.

The invention also comprises an improvement in the known method of parenterally administering clinical dextran having a weight average molecular weight ($\overline{M}_w$) within the range 30,000 to 80,000 to mammals, including man, which improvement comprises administering parenterally to the mammal, closely prior to or contemporaneously with the administration of said clinical dextran, a sterile aqueous solution for parenteral administration containing 0.01 to 35 g (e.g. 0.2 to 30 g) per 100 ml solution of a mixture of isomalto-oligosaccharides as specified above in an amount effective for blocking antibodies directed against dextran and occurring in said mammal.

According to a preferred embodiment, said mixture is administered contemporaneously with and in the same solution as said dextran.

As should be recognized by the man of ordinary skill in the art the isomalto-oligosaccharides will be excreted with the urine. For that reason, when the solution of the mixture of isomalto-oligosaccharides is administered prior to the administration of the solution of clinical dextran, the interval between the two administrations should not be extended too much and suitably should not exceed one hour and preferably lies within the range of 10–0 minutes.

Generally, the amount of the isomalto-oligosaccharide mixture given parenterally for this purpose will be 0.001 to 0.3 g of said mixture per kg bodyweight, preferably 0.005 to 0.1 g per kg bodyweight, for example 0.01 to 0.05 g per kg bodyweight.

The invention is further illustrated by the following examples.

EXAMPLE 1

(A) 10.5 l of 8.6 N HCl were added to 1000 l of an aqueous solution containing 400 kg of dextran fraction of $\overline{M}_w = 17,000$ (obtained from native dextran from Leuconostoc mesenteroides, strain NRRL B-512, by hydrolysis and fractionation) at 85° C. Hydrolysis was allowed to proceed 30 h at 85° C. whereafter the solution was cooled and neutralised by adding an aqueous solution of sodium hydroxide. A first fraction was precipitated at about 20° C. by the addition of 4300 l of 90% ethanol. The precipitated fraction was recovered and dissolved in water to a volume of the solution of 500 l and the solution was then filtered with 10 kg of active carbon. A new fraction was precipitated at 20° C. from the filtrate thus obtained by the addition of 2000 l of 90% ethanol. The precipitated fraction was dissolved in water to a volume of the solution of 420 l and the solution was filtered with 20 kg of active carbon. After filtration and spray-drying about 100 kg of substance were obtained in the form of a white powder.

(B) 10.5 of 8.6 N HCl were added to 1000 l of an aqueous solution containing 265 kg of dextran fraction of $\overline{M}_w = 17,000$ at 88° C. Hydrolysis was allowed to proceed 24 h at 88° C. whereafter the solution was cooled and neutralized by adding an aqueous solution of sodium hydroxide. The solution was then filtered with 10 kg of active carbon and concentrated to a volume of 440 l. A first fraction was precipitated at about 20° C. by the addition of 1750 l of 90% ethanol. The precipitated fraction was recovered and dissolved in water to a volume of the solution of 550 l and filtered with 5 kg of active carbon. The solution was then concentrated to a volume of 325 l and a new fraction was precipitated at about 20° C. by the addition of 1300 l of 90% ethanol. The precipitated fraction was recovered and dissolved in water to a volume of the solution of 270 l. A new fraction was precipitated by the addition of 1080 l 90% ethanol. The precipitated fraction was recovered and dissolved in water to a volume of the solution of 500 l and the solution was then filtered with 5 kg of active carbon. After filtration and spray-drying about 100 kg of substance were obtained in the form of a white powder.

(C) A substance was prepared in a manner analogous to (B) above but hydrolysing for 25 h at 88° C. After the last filtration and the spray-drying about 100 kg of substance were obtained in the form of a white powder.

(D) One part by weight each of the substances obtained according to (A), (B) and (C) were thoroughly mixed to a homogeneous substance mixture. Analysis showed that per 100 g of substance the mixture consisted of 96 g of an isomalto-oligosaccharide mixture, 3 g of glucose and 1 g of sodium chloride. Chromatographic analysis showed that the isomalto-oligosaccharide mixture consisted of 7% (this percentage as well as those below being percent by weight calculated on the total weight of the isomalto-oligosaccharide mixture) of isomaltose, 11% of isomaltotriose, 15% of isomaltotetraose, 16% of isomaltopentaose, 14% of isomaltohexaose, 11% of isomaltoheptaose, 7% of isomaltooctaose, 5% of isomaltononaose and 14¹ % of isomalto-oligosaccharides of 10 or more glucose units (12% consisting of oligosaccharides of 10 to 14 glucose units and 2% consisting of oligosaccharides of 15 to 20 glucose units). $\overline{M}_w$ of the isomalto-oligosaccharide mixture was 1020, as estimated with gel chromatographic analysis.

EXAMPLE 2

A solution containing 15 g of carbohydrate and 0.6 g of sodium chloride per 100 ml solution was prepared by dissolving appropriate amounts of the carbohydrate-containing substance of Example 1 D and sodium chloride in distilled pyrogen-free water at 90° C. The solution was filtered and filled on 10 ml and 500 ml glass bottles which then were sealed and heat-sterilized at 120° C. for 35 minutes.

EXAMPLE 3

(A) A solution containing 6 g of Dextran 70, 0.8 g of sodium chloride and 0.6 g of carbohydrate of Example 1 D per 100 ml solution was prepared by dissolving appropriate amounts of the carbohydrate-containing substance of Example 1 D, sodium chloride and Dextran 70 in distilled pyrogen-free water. The solution was filtered and filled on 500 ml and 100 ml glass bottles which were then sealed and heat-sterilized at 120° C. for 35 minutes.

(B) A solution was prepared as in (A) above but with 0.3 g of carbohydrate of Example 1 D per 100 ml instead of 0.6 g.

EXAMPLE 4

0.6 parts by weight of the carbohydrate substance as prepared in Example 1 D in powder form were thoroughly mixed with 6 parts by weight of Dextran 70 in powder form. The substance obtained is suitable for preparation of infusion solutions. Such a solution can be prepared for example as follows: 6.6 kg of said substance and 0.8 kg of sodium chloride are dissolved in distilled pyrogen-free water to a solution volume of 100 liter. The solution is filtered and filled on 500 ml glass bottles which then are sealed and heat-sterilized at 120° C. for 34 minutes.

EXAMPLE 5

An aqueous solution was prepared which contained 24 g of Dextran 40 and 1.2 g of the carbohydrate substance as prepared in Example 1 D per 100 ml solution. The solution was filtered and spray-dried. The powder thus obtained is suitable for the preparation of infusion solutions. Such a solution can be prepared for example as follows: 10.5 kg of said powder and 0.8 kg of sodium chloride are dissolved in distilled pyrogen-free water to a solution volume of 100 liter. The solution is filtered and filled on 500 ml glass bottles which then are sealed and heat-sterilized at 120° C. for 35 minutes.

What is claimed is:

1. In the known method of parenterally administering to mammals, including man, clinical dextran having a weight average molecular weight ($\overline{M}_w$) within the range 30,000 to 80,000, the improvement which comprises administering parenterally to the mammal, closely prior to or contemporaneously with the administration of said clinical dextran, an effective amount of a sterile aqueous solution for parenteral administration containing 0.02 to 30 g per 100 ml solution of a mixture of isomalto-oligosaccharides comprising
   (a) 0–15 percent by weight of isomaltose,
   (b) 20–65 percent by weight of isomaltotriose, isomaltotetraose and isomaltopentaose, each of these oligosaccharides being present in an amount of at least 5 percent by weight and at most 25 percent by weight,
   (c) 20–65 percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight,
   0–30 percent by weight of said mixture being isomalto-oligosaccharides of 10 to 20 glucose units and 0–10 percent by weight of said mixture being isomalto-oligosaccharides of 15 to 20 glucose units,
   the percentages being calculated on the total weight of the mixture of isomalto-oligosaccharides.

2. A method as set forth in claim 1 wherein said sterile aqueous solution contains 0.2 to 30 g of said mixture per 100 ml of solution.

3. A method as set forth in claim 1 wherein said mixture is administered contemporaneously with and in the same solution as said dextran.

4. A method as set forth in claim 1 wherein said mixture comprises 2–10 percent by weight of isomaltose.

5. A method as set forth in claim 1 wherein said mixture comprises 25–55 percent by weight of isomaltotriose, isomaltotetraose and isomaltopentaose.

6. A method as set forth in claim 1, wherein said mixture comprises 25–55 percent by weight of isomaltohexaose, isomaltoheptaose, isomaltooctaose and isomaltononaose.

7. A method as set forth in claim 1, wherein said mixture comprises 5–20 percent by weight of isomalto-oligosaccharides of 10 to 20 glucose units, 0–7 percent by weight of said mixture consisting of isomalto-oligosaccharides of 15 to 20 glucose units.

8. A method of improving clinical dextran having a weight average molecular weight ($\overline{M}_w$) within the range 30,000 to 80,000 with respect to side effects on parenteral administration, characterized in that said clinical dextran is admixed with a mixture of isomalto-oligosaccharides comprising
   (a) 0–15 percent by weight of isomaltose,
   (b) 20–65 percent by weight of isomaltotriose, isomaltotetraose and isomaltopentaose, each of these oligosaccharides being present in an amount of at least 5 percent by weight and at most 25 percent by weight,
   (c) 20–65 percent by weight of isomaltohexaose, isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight,
   0–30 percent by weight of said mixture being isomalto-oligosaccharides of 10 to 20 glucose units and 0–10 percent by weight of said mixture being isomalto-oligosaccharides of 15 to 20 glucose units,
   the percentages being calculated on the total weight of the mixture of isomalto-oligosaccharides,
   the proportions between said mixture of isomalto-oligosaccharides and said clinical dextran being 1 part by weight of said mixture of 0.5 to 500 parts by weight of said clinical dextran.

9. A method according to claim 8 wherein said mixture comprises 2–10 percent by weight of isomaltose.

10. A method according to claim 8 wherein said mixture comprises 25–55 percent by weight of isomaltotriose, isomaltotetraose and isomaltopentaose.

11. A method according to claim 8 wherein said mixture comprises 25–55 percent by weight of isomaltohexaose, isomaltoheptaose, isomaltooctaose and isomaltononaose.

12. A method according to claim 8 wherein said mixture comprises 5–20 percent by weight of isomalto-oligosaccharides of 10 to 20 glucose units, 0–7 percent by weight of said mixture consisting of isomalto-oligosaccharides of 15 to 20 glucose units.

13. A sterile aqueous solution for parenteral administration characterized in that it contains 0.02 to 30 g per 100 ml solution of a mixture of isomalto-oligosaccharides, said mixture of oligosaccharides comprising
   (a) 0–15 percent by weight of isomaltose,
   (b) 20–65 percent by weight of isomaltotriose, isomaltotetraose and isomaltopentaose, each of these oligosaccharides being present in an amount of at least 5 percent by weight and at most 25 percent by weight, (c) 20–65 percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight, 0–30 percent by weight of said mixture being isomalto-oligosaccharides of 10 to 20 glucose units and 0–10 percent by weight of said mixture being isomalto-oligosaccharides of 15–20 glucose units, the percentages being calculated on the total weight of the mixture of isomalto-oligosaccharides, and in that it also contains 2 to 12 g of clinical dextran per 100 ml solution, said clinical dextran having a weight average molecular weight $\overline{M}_w$ within the limits 30,000 to 80,000.

14. A sterile aqueous solution according to claim 13 wherein the solution contains 0.02 to 10 g of the isomalto-oligosaccharide mixture per 100 ml solution.

15. A sterile aqueous solution according to claim 14 wherein the solution contains 0.2 to 10 g of the isomalto-oligosaccharide mixture per 100 ml solution.

16. A sterile aqueous solution according to claim 13 wherein the solution contains less than 0.4 g of dextran molecules in the molecular weight range of 3,000 to 10,000 per 100 ml solution.

17. A sterile aqueous soltuion according to claim 13 wherein the isomalto-oligosaccharide mixture in the solution comprises 2–10 percent by weight of isomaltose.

18. A sterile aqueous solution according to claim 13 wherein the isomalto-oligosaccharide mixture in the solution comprises 25–55 percent by weight of isomaltotriose, isomaltotetraose and isomaltopentaose.

19. A sterile aqueous solution according to claim 13 wherein the isomalto-oligosaccharide mixture in the solution comprises 25–55 percent by weight of isomaltohexaose, isomaltoheptaose, isomaltooctaose and isomaltononaose.

20. A sterile aqueous solution according to claim 13 wherein the isomalto-oligosaccharide mixture in the solution comprises 5–20 percent by weight of isomalto-oligosaccharides of 10 to 20 glucose units and 0–7 percent by weight of said mixture consisting of isomalto-oligosaccharides of 15 to 20 glucose units.

21. A sterile aqueous solution for parenteral administration characterized in that it contains 0.02 to 30 g per 100 ml solution of a mixture of isomalto-oligosaccharides, said mixture of oligosaccharides comprising (a) 0–15 percent by weight of isomaltose,
(b) 20–65 percent by weight of isomaltotriose, isomaltotetraose and isomaltopentaose, each of these oligosaccharides being present in an amount of at least 5 percent by weight and at most 25 percent by weight,
(c) 20–65 percent by weight of isomaltohexaose, isomaltoheptaose, isomaltooctaose and isomaltononaose, each of isomaltohexaose and isomaltoheptaose being present in an amount of at least 5 percent by weight and at most 25 percent by weight and the total amount of isomaltooctaose and isomaltononaose being at least 5 percent by weight and at most 25 percent by weight, 0–30 percent by weight of said mixture being isomalto-oligosaccharides of 10 to 20 glucose units and 0–10 percent by weight of said mixture being isomalto-oligosaccharides of 15 to 20 glucose units, the percentages being calculated on the total weight of the mixture of isomalto-oligosaccharides.

22. A sterile aqueous solution according to claim 21 wherein the content of the mixture of isomalto-oligosaccharides is 0.2 to 30 g per 100 ml solution.

23. A sterile aqueous solution according to claim 21 wherein the isomalto-oligosaccharide mixture in the solution comprises 2–10 percent by weight of isomaltose.

24. A sterile aqueous solution according to claim 21 wherein the isomalto-oligosaccharide mixture in the solution comprises 25–55 percent by weight of isomaltotriose, isomaltotetraose and isomaltopentaose.

25. A sterile aqueous solution according to claim 21 wherein the isomalto-oligosaccharide mixture in the solution comprises 25–55 percent by weight of isomaltohexaose, isomaltoheptaose, isomaltooctaose and isomaltononaose.

26. A sterile aqueous solution according to claim 21 wherein the isomalto-oligosaccharide mixture in the solution comprises 5–20 percent by weight of isomalto-oligosaccharides of 10 to 20 glucose units, 0–7 percent by weight of said mixture consisting of isomalto-oligosaccharides of 15 to 20 glucose units.

* * * * *

UNITED STATES PATENT AND TRADEMARK OFFICE

CERTIFICATE EXTENDING PATENT TERM
UNDER 35 U.S.C. 156

Patent No.    : 4,201,772

Dated         : May 6, 1980

Inventor(s)   : Ingelman et al.

Patent Owner  : Pharmacia Aktiebolag

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

468 DAYS with all rights pertaining thereto as provided by 35 USC 156(b).

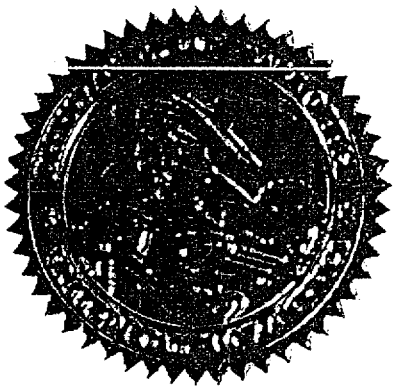

I have caused the seal of the Patent and Trademark Office to be affixed this Eighteenth day of April, 1986.

Donald J. Quigg

Assistant Secretary and Commissioner of Patents and Trademarks